(12) United States Patent
Soliz et al.

(10) Patent No.: US 10,610,098 B1
(45) Date of Patent: Apr. 7, 2020

(54) GENERALIZED RETINAL IMAGE SCREENING SYSTEM (GRIS)

(71) Applicant: VisionQuest Biomedical LLC, Albuquerque, NM (US)

(72) Inventors: Peter Soliz, Albuquerque, NM (US); Jeremy Benson, Albuquerque, NM (US); Trilce Estrada, Albuquerque, NM (US)

(73) Assignee: VISIONQUEST BIOMEDICAL LLC, Albuquerque, NM (US)

( * ) Notice: Subject to any disclaimer, the term of this patent is extended or adjusted under 35 U.S.C. 154(b) by 0 days.

(21) Appl. No.: 15/951,036

(22) Filed: Apr. 11, 2018

Related U.S. Application Data

(60) Provisional application No. 62/484,243, filed on Apr. 11, 2017.

(51) Int. Cl.
  *A61B 3/00* (2006.01)
  *A61B 3/14* (2006.01)
  (Continued)

(52) U.S. Cl.
  CPC .......... *A61B 3/14* (2013.01); *A61B 3/12* (2013.01); *G06K 9/6269* (2013.01);
  (Continued)

(58) Field of Classification Search
  CPC ......... A61B 3/14; A61B 3/102; A61B 3/0025; A61B 3/12; A61B 3/1025; A61B 3/0008; A61B 3/1005; A61B 3/113; A61B 3/1225; A61B 3/0058; A61B 3/107; A61B 3/117; A61B 3/13; A61B 3/1015; A61B 3/145; A61B 3/10; A61B 3/0041; A61B 3/152; A61B 3/103; A61B 3/0033; A61B 3/0075;
  (Continued)

(56) References Cited

U.S. PATENT DOCUMENTS

| 8,515,201 B1 | 8/2013 | Murray Herrera et al. |
| 2015/0351722 A1* | 12/2015 | Chen ............ A61B 8/485 600/427 |

(Continued)

OTHER PUBLICATIONS

"National Eye Institute: Statistics and Data", https://nei.nih.gov/eyedata, Accessed Nov. 21, 2019.
(Continued)

*Primary Examiner* — Collin X Beatty
*Assistant Examiner* — Grant A Gagnon
(74) *Attorney, Agent, or Firm* — Peacock Law P.C.; Janeen Vilven

(57) ABSTRACT

Embodiments of the present invention provide a system and method to automatically screen images from a plurality of fundus cameras for a plurality of retinal diseases. The system comprises stacked autoencoders, amplitude modulation-frequency modulation filters, and artificial neural networks. An embodiment of the present invention uses a multi-class classifier, such as a support vector machine (multi-class SVM) classifier, to determine a plurality of retinal pathologies. An exemplary embodiment of the present invention is validated on a proprietary database of thousands of images (for example over 250,000 retinal images) from multiple cameras, ranging from the table-top fundus cameras to portable hand-held cameras.

16 Claims, 8 Drawing Sheets

(51) Int. Cl.
  *A61B 3/12* (2006.01)
  *G06T 7/00* (2017.01)
  *G06K 9/62* (2006.01)
  *G16H 30/00* (2018.01)

(52) U.S. Cl.
  CPC ............ *G06T 7/0012* (2013.01); *G16H 30/00* (2018.01); *G06T 2207/30041* (2013.01)

(58) Field of Classification Search
  CPC ......... A61B 3/0091; A61B 3/112; A61B 3/18; A61B 5/0066; A61B 2576/02; A61B 3/005; A61B 3/101; A61B 3/1208; A61B 3/1241; A61B 3/125; A61B 3/158; A61B 5/0013; A61B 2560/0475; A61B 3/00; A61B 3/0083; A61B 3/028; A61B 3/032; A61B 3/11; A61B 3/111; A61B 3/1233; A61B 3/132; A61B 5/0075; A61B 5/489; A61B 2017/00716; A61B 2503/10; A61B 2503/20; A61B 2560/0223; A61B 2560/0228; A61B 2560/0233; A61B 2560/0266; A61B 2560/0271; A61B 3/0016; A61B 3/024; A61B 3/063; A61B 3/08; A61B 3/1035; A61B 3/1173; A61B 3/1176; A61B 3/1216; A61B 3/135; A61B 3/15; A61B 3/154; A61B 3/156; A61B 5/0022; A61B 5/0059; A61B 5/02416; A61B 5/0261; A61B 5/1075; A61B 5/1079; A61B 5/1103; A61B 5/1114; A61B 5/1116; A61B 5/1124; A61B 5/1128; A61B 5/1176; A61B 5/1455; A61B 5/165; A61B 5/18; A61B 5/4821; A61B 5/4848; A61B 5/486; A61B 5/6803; A61B 5/7275; A61B 5/7425; A61B 8/10; A61B 90/20; G06T 2207/30041; G06T 7/0012; G06T 2207/10101; G06T 7/0016; G06T 2200/24; G06T 7/74; G06T 11/003; G06T 2207/10016; G06T 2207/10056; G06T 2207/20016; G06T 2207/20056; G06T 2210/41; G06T 3/4038; G06T 7/0014; G06T 7/11; G06T 7/246; G06T 7/30; G06T 7/32; G06T 7/337; G06T 7/64; G06K 9/00604; G06K 9/00214; G06K 9/00597; G06K 9/6201; G16H 50/30
  USPC .......................................................... 351/206
  See application file for complete search history.

(56) References Cited

U.S. PATENT DOCUMENTS

2018/0084988 A1* 3/2018 Chakravorty ........ A61B 3/0025
2019/0043193 A1* 2/2019 Odaibo ................. G06T 7/0014

OTHER PUBLICATIONS

Abramoff, M. D., et al., "Improved Automated Detection of Diabetic Retinopathy on a Publicly Available Dataset Through Integration of Deep Learning", Invest Ophthalmol Vis Sci, vol. 57, No. 13, Oct. 2016, 5200-5206.
Age-Related Eye Disease Study, Research Group , "A randomized, placebo-controlled, clinical trial of high-dose supplementation with vitamins C and E, beta carotene and zinc for age-related macular degeneration and vision loss", AREDS report No. 8, Arch Ophthalmol, vol. 126, No. 9, 2008.
Agurto, C. , et al., "Multiscale AM-FM Methods for Diabetic Retinopathy Lesion Detection", IEEE Trans. Med. Imaging, vol. 29, No. 2, 2010, 502-512.
Al-Rawi, M. , et al., "An improved matched filter for blood vessel detection of digital retinal images", Comput. Biol. Med., vol. 37, No. 2, 2007, 262-267.
Bengio, Y. , "Learning deep architectures for AI", Foundations and Trends in Machine Learning, vol. 2, No. 1, 2009, 1-127.
Bhaskaranand, M. , et al., "Automated Diabetic Retinopathy Screening and Monitoring Using Retinal Fundus Image Analysis", Journal of Diabetes Science and Technology, vol. 10, No. 2, 2016, 254-261.
Chader, G. J., et al., "Preface: the Aging Eye: Normal Changes, Age-Related Diseases, and Sight-Saving Approaches", Investigative Ophthalmology & Visual Science, vol. 54, No. 14, 2013, ORSF1-ORSF4.
Chasan, J. E., et al., "Effect of a teleretinal screening program on eye care use and resources", JAMA Ophthalmol., vol. 132, No. 9, 2014, 1045-1051.
Fu, H. , et al., "Retinal vessel segmentation via deep learning network and fully-connected conditional random fields", IEEE 13th International Symposium on Biomedical Imaging (ISBI), 2016.
Goatman, K. , et al., "Assessment of Automated Disease Detection in Diabetic Retinopathy Screening Using Two-Field Photography", PLoS One, vol. 6, No. 12, 2011.
Guishan, V. , et al., "Development and Validation of a Deep Learning Algorithm for Detection of Diabetic Retinopathy in Retinal Fundus Photographs", JAMA, vol. 316, No. 22, 2016, 2402-2410.
Hsu, C. , et al., "A comparison of methods for multiclass support vector machines", IEEE Trans Neural Netw, vol. 13, No. 2, 2002, 415-425.
Krizhevsky, A. , "ImageNet Classification with Deep Convolutional Neural Networks", Advances in Neural Information Processing Systems 25, Curran Associates, Inc., 2012, 1097-1105.
Liew, G. , et al., "A Comparison of the Causes of Blindness Certifications in England and Wales in working age adults (16-64 years), 1999-2000 with 2009-2010", BMJ Open, vol. 4, No. 2, 2014, 1-6.
Maninis, K. , et al., "Deep Retinal Image Understanding", CoRR, vol. abs/1609.01103, 2016.
Quellec, G. , et al., "Detection of lesions in retina photographs based on the wavelet transform", Proceedings of the 28th IEEE EMBS Annual International Conference, New York, NY, Aug. 30-Sep. 3, 2006, 2618-2621.
Quellec, G. , et al., "Optimal Wavelet Transform for the Detection of Microaneurysm in Retina Photographs", IEEE Transactions on Medical Imaging, vol. 27, 2008, 1230-1241.
Ribeiro, L. , et al., "Screening for Diabetic Retinopathy in the Central Region of Portual. Added Value of Automated Disease/No Disease' Grading", Eur J Ophthalmol, vol. 25, No. 3, 2015, e7-e30.
Sofka, Michal , et al., "Retinal vessel extraction using multiscale matched filters confidence and edge measures", IEEE Transactions on Medical Imaging, vol. 25, No. 12, 2005.
Tang, Y. , "Deep learning using linear support vector machines", In Workshop on Representational Learning, ICML, 2013.
Tufail, A. , et al., "An observational study to assess if automated diabetic retinopathy image assessment software aan replace one or more steps of manual imaging grading and to determine their cost-effectiveness", NIHR Journals Library, vol. 20, Issue 92, Dec. 2016.
Vallabha, Deepika , et al., "Automated detection and classification of vascular abnormalities in diabetic retinopathy", Asilomar Conference on Signals, Systems & Computers, No. 38, Pacific Grove, CA., 2004.
Varma, R. , et al., "Visual Impairment and Blindness in Adults in the United States Demographic and Geographic Variations from 2015 to 2050", JAMA Ophthalmol., vol. 134, No. 7, Jul. 2016, 802-809.
Vincent, P. , et al., "Extracting and Composing Robust Features with Denoising Autoencoders", Twenty-fifth International Conference on Learning, 2008.
Walter, T. , et al., "A Contribution of Image Processing to the Diagnosis of Diabetic Retinopathy-Detection of Exudates in Colour

(56) References Cited

OTHER PUBLICATIONS

Fundus Images of the Human Retina", IEEE Transactions on Medical Imaging, vol. 21, No. 10, Oct. 2002, 1236-1243.
"Prevalence of Adult Vision Impairment and Age-Related Eye Diseases in America,", https://nei/nih.gov/eyedata/adultvision_usa, Downloaded Nov. 27, 2019.

* cited by examiner

0000110000000011

1011111110011111

GENERALIZED RETINAL IMAGE SCREENING SYSTEM (GRIS)

CROSS-REFERENCE TO RELATED APPLICATIONS

This application claims priority to and the benefit of the filing of U.S. Provisional Application No. 62/484,243 entitled "Generalized Retinal Image Screening System (GRIS)", filed on Apr. 11, 2017, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable

BACKGROUND

There are nearly 40 million adults in the US that have one of the sight-threatening eye diseases [1]. Direct medical costs in the United States due to the major eye diseases are estimated at over $14.5 billion [2]. The major eye diseases affect a person's quality of life. By 2050, the estimated number of people affected by eye diseases is expected to double [3,4]. With the growing increase in prevalence of eye diseases and shortage of eyecare specialists, automatic screening and detection of these pathologies is becoming vital. Savings from early detection and treatment through screening programs are widely documented [5,6]. Automatic retinal screening software gives patients access to eyecare at locations other than the specialist's clinics. A major hurdle to successfully implementing automatic screening is the need for scalability such that a single software program can be applied to images from any fundus camera and in the detection of any retinal disease.

Automatic (computer-based) screening at the point of service, promises to address the problems of access and compliance. However, this promise has not been realized in large part due to a two-way market segmentation. One, the market is divided into several retinal camera brands and models, resulting in a wide spectrum of image characteristics. Two, there is a selection of automatic screening algorithms that operate not only with a specific camera, but also for a single eye disease, resulting in a significant interoperability problem. Scaling to meet the demand for eye screening across images from a plurality of fundus cameras, for a plurality of retinal diseases, and automatic screening software represents a major hurdle.

In a recent study Tufail et al. [7] tested three diabetic retinopathy (DR) automatic screening algorithms developed by various groups [8,9,10] on retinal images obtained in a National Health Service setting in the UK. The performance of the algorithms was less effective than their previously published performance in other datasets [9,10]. This notable degradation in performance can be attributed to differences in the image characteristics (camera) used in the training set for their respective models and the images (from different model cameras) used to test the three algorithms, among other factors. The algorithms need an expensive retraining phase to deal with the distinct characteristics of different camera models.

Deep learning (DL) algorithms have been proposed for addressing the need for scaling and enhancing automatic screening algorithms. There are a variety of challenges inherent to the design of deep learning networks. For example, when designing deep learning networks, one must choose the number of layers and decide on their architecture. During training, hyperparameters, such as the learning rate, batch size, and iterations must also be chosen. These requirements incur the challenge of expensive and extensive training iterations. Multiscale amplitude-modulation frequency modulation (AM-FM) system and methods of amplitude-modulation frequency-modulation (AM-FM) demodulation for image and video processing. U.S. Pat. No. 8,515,201 B1. Methods have been shown to be successful in producing comprehensive sets of features for discriminating between normal and pathological retinal images [11], and so, shall be used to expedite the learning process.

DL has been applied in ophthalmology [12,13,14], but not in a manner as taught herein. The value and capabilities of DL are being recognized in the area of computer-based medical image classification for detection of pathology in various imaging modalities. These studies demonstrate that DL approaches yield better performance than traditional image processing and classification methods [13,15].

Abramoff et al., reported using DL to detect DR [13]. Their database consisted of 1,748 images obtained from one camera and applied to only one retinal disease, DR. Although the results of this study are encouraging, this study focuses on only one camera model and does not address a plurality of retinal disease detection. Recently, a study published by Gulshan et al., [16] used DL for DR detection, which used 128,175 images from six different types of cameras for training Said study does not introduce a camera not used in the training to test the scalability of their DL methodology.

An autoencoder is an artificial neural network (ANN) model that learns parameters for a series of nonlinear transformations that encodes the input into a lower dimensional space or feature set and decodes a reconstructed output, with the goal of minimizing the differences between the original input and the decoded output. An autoencoder produces an intermediate representation of the input that minimizes information loss [17,18]. The encoding process transforms the input data into a different data representation suitable for computer processing but not for human mental processes due to the volume, complexity (high dimensionality) and timeframe. The decoding process by a computer processor the decoding process simply reconstructs the input to the encoder, with some loss, and may or mot not be suitable for human analyses. The complexity of the encoding/decoding process and the speed required to generate results that are compatible with current clinical flow prohibit a human from processing the same volume of data of the same complexity during the same time period.

The extraction of features from a retinal image is commonly the basis for most automatic classification system. Morphological methods [19], Gabor filters [20], Wavelet transforms [21,22] and Match filters [23, 24] are the most popular methods for the feature extraction. The latter have been widely used on retinal images for vessels segmentation. ANN like stacked autoencoders or convolutional neural networks are designed to learn useful filters, which bring out key features from the image. Combining these learning methods with the AM-FM filters will enhance the feature space and accelerate the autoencoding process.

BRIEF DESCRIPTION OF EMBODIMENTS OF THE PRESENT INVENTION

One embodiment of the present invention provides for a method of standardizing a plurality of data sets obtained from an arbitrary number of data capturing devices comprising the steps of processing a first data set obtained from a first data capturing device with a first feature extraction process to produce a first processed feature set wherein the first data capturing device captures a first data set at a low fidelity level. The first processed feature set is encoded to produce a first encoded feature set. A second data set is processed from a second data capturing device with a second feature extraction process which may be the same or different from the first feature extraction process (for example may comprise AMFM) to produce a second processed feature set wherein the second data capture device captures the second data set at a high fidelity level as compared to the low fidelity level of the first data set. The second processed feature set is encoded to produce the second encoded feature set wherein the second encoded feature set is constrained by the first encoded feature set such that the second encoded feature set is of a same or greater dimensionality as compared to the first encoded feature set. For example, the first data capture device and or the second data capture device may be an imager for example a digital camera that obtains digital images. The fidelity level is determined by for example characteristics selected from one or more of the following pixel count, resolution, dimensionality, optics, flash intensity and modulation transfer function for example. The encoding step may compress the first processed feature set or the second processed feature set into an encoded space that is in a lower dimension than the corresponding first processed feature set or second processed feature set. The processing step may comprise reducing the dimensionality of the first data set wherein the dimensionality includes a row, a column and a depth of a numerical matrix. Further, the encoding process may be iterative such that a loss function is sent as an input parameter to a subsequent iteration of the encoding step.

In another embodiment, a method of standardizing a plurality of digital images of a retina for use with an automated retinal disease classifier comprises processing a first digital retinal image obtained from a first imager with a first feature extraction process to produce a first processed feature set wherein the first data imager a first digital retinal image data set at a low fidelity level. The first processed feature set is encoded to produce a first encoded feature set. A second digital retinal image obtained from a second imager is processed with a second feature extraction process which may be the same or different from the first feature extraction process to produce a second processed feature set wherein the second imager captures the second digital retinal image at a high fidelity level as compared to the low fidelity level of the first data set. The second processed feature set is encoded to produce a second encoded feature set wherein the second encoded feature set is constrained by the first encoded feature set such that the second encoded feature set is of a same or greater dimensionality as compared to the first encoded feature set to standardize the first retinal image and the second retinal image. Further, this process can be repeated with retinal images obtained from additional digital imagers having a fidelity level that is the same or different from the first imager and the second imager. The first encoded feature set and the second encoded feature set is classified for the presence or absence of a retinal disease via an automated classifier such that the disease is classified with a sensitivity and/or specificity of about 50%, 60%, 70%, or 80% or better.

In one embodiment of the present invention provides for steps that include: (i) feature extraction using stacked autoencoders and AM-FM; (ii) classification of normal and retinal pathologies using the extracted features. In this embodiment, there is no requirement for segmentation of individual lesions by the ophthalmologist or any labelling, whatsoever. Autoencoding is an unsupervised approach to find representative features. After the network is complete, available labels or markings on particular images can lead to identifying known groups or clusters.

One aspect of one embodiment of the present invention provides an automated approach based on combining a plurality of stacked autoencoders to create a deep neural network for feature extraction. The layering is done to create a span of cameras with different resolution/quality of images, ranging from state-of-art fundus cameras to portable hand-held retinal cameras, in decreasing order of resolution/quality from top to bottom of the stack. Each layer of the stack is its own, individual AM-FM-enhanced stacked autoencoder. In the next section, we detail different components of the system.

One aspect of one embodiment of the present invention uses one or more classifiers to detect a plurality of retinal diseases. Autoencoding does not need labels of any sort on the image, as the data itself serves to be the 'ground truth' for each image. Any existing labels that we have on images can be used after the fact to help us identify what the different groups are (i.e., after the smallest hidden feature space is calculated for each image, they will group or cluster into different bins/buckets.)

One aspect of one embodiment of the present invention uses AM-FM filters as the first module of each stacked autoencoder architecture to create a deep neural network for feature extraction. In another aspect of the present invention, AM-FM filter is used in one or more subsequent layers or autoencoder.

One aspect of one embodiment of this present invention is implemented in primary care physician's clinics, screening centers, eye care centers etc. The fundus images obtained are either stored onsite or transferred via an electronic communication medium such as but not limited to a local area network, a wide area network, or the internet.

One aspect of one embodiment of this present invention comprises onsite computing and processing. Yet another embodiment of the present invention comprises remote computing and processing such as the systems referred to as cloud computing.

One aspect of one embodiment of this present invention generates a report for each patient to be sent to primary care physician, ophthalmologist or referring physician. In one aspect of one embodiment of this present invention, the output of the classifier is binary, triaging to referral and non-referral classes. In another aspect of the present invention, the output of the classifier is a continuous scale that comprises one or more thresholds.

One aspect of one embodiment of this present invention can be implemented onsite. Another aspect of this embodiment can be implemented as a telemedicine screening system.

One aspect of one embodiment of the present invention provides a universal framework for conversion of non-compatible images to be used with a plurality of automatic screening algorithms.

One aspect of one embodiment of the present invention provides a system to triage eyes for referral based on the eye pathology present in retinal images.

Additional aspects to this framework include: 1) encoding the data, ensures the efficient storage and indexing of data with much higher throughput, 2) the encoded data can be decoded with a framework as disclosed herein, for example exclusively, so it provides additional form of security while transmitting the data, e.g. in a telemedicine setting.

One aspect of one embodiment of this present invention uses a classifier, which can be a softmax activation function where the final layer's hidden feature space behaves as input.

One aspect of one embodiment of the present invention uses an integrated algorithm to detect major eye diseases, with a model camera with imaging properties that are acceptable for obtaining images of an eye under examination for detection of eye disease, which features will help achieve greater cost effectiveness for retinal screening.

One aspect of one embodiment of this present invention uses mydriatic or non-mydriatic color fundus images. It shall be evident to others skilled in the art that this present invention can also be used with including but not limited to other retinal imaging modalities like red free, optical coherence tomography (OCT), scanning laser ophthalmoscope (SLO) etc.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION

As used herein "a", "an" and "the" mean one or more unless clearly indicated otherwise.

As used here in "segmentation" means annotation of data (e.g. images) whether computer based or manual annotation to a fine grained (e.g., individual pixel(s), voxel(s), region, boundary, etc.) level of detail. For example, a picture of a tree in which the pixel values surrounding the perimeter of branches are marked and noted and in the same picture, the grass and clouds can all be segmented. Typically, in manual segmentation, the class of the object *e.g., branch (is noted and marked). In some computer-based segmentation algorithms, the class of the object is unknown, and the segmentation simply aims to find distinct borers or boundaries within the image e.g., an edge detector).

As used herein "labeling" means a high level that is to say, not at the level of marking and identifying pixel coordinate subspaces within the image) marking of data (e.g., an image) and is not a fine-grained piece of information. As an example, consider a picture of a beach; the label would be 'beach' or 'ocean' but would not have any information or annotation for location (e.g., the pixel coordinates) of any labels.

As used herein "unsupervised learning" means any machine learning process that handles data without segmentation or labels (i.e., all of the data is unknown)

As used herein "supervised learning" means any machine learning process that handles data with segmentation or labels (i.e., all of the data has some sort of known element)

As used herein "semi-supervised learning" means any machine learning process that works with partially labeled/known data.

One embodiment of a generalized retinal image screening system presented herein consists of two main processing phases: feature extraction using stacked autoencoders (SAE) and classification.

Figure 1:
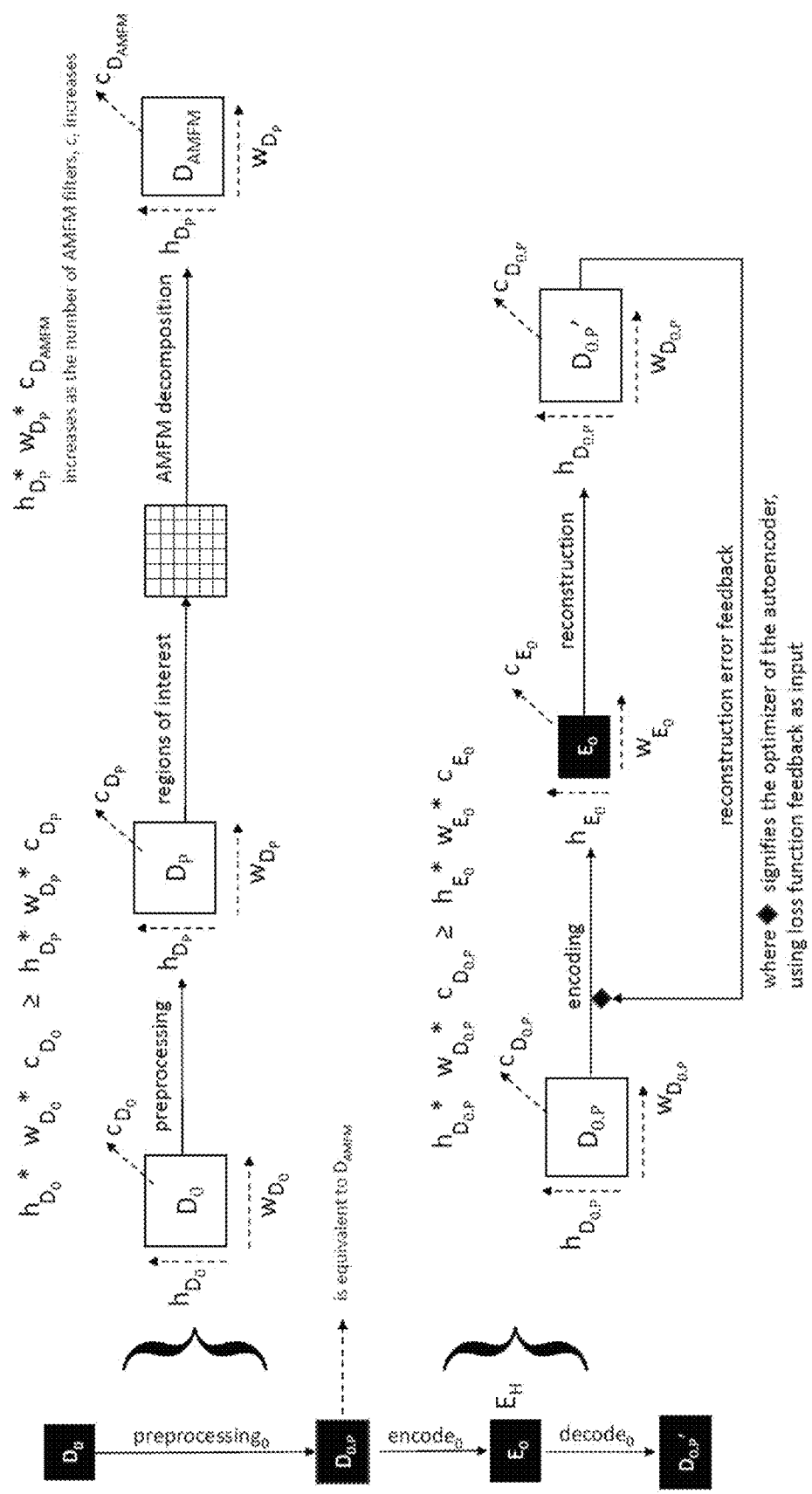
FIG. 1 illustrates one embodiment of a system for processing data sets obtained by a data capture device using a feature extraction step for processing the data sets before further processing for standardizing the data sets obtained from separate and different data capture devices having different fidelity levels.

Referring now to FIG. 1, a top layer of one embodiment of the present invention provides for preprocessing of a dataset from Dataset D (in this case, an initial preprocessing that may or may not reduce the dimensionality of the data, in terms of rows, columns, and depth of a numerical matrix) into preprocessed data $D_P$. The preprocessed data $D_P$ is then sent through an arbitrary number of preprocessing steps, such as (in this example) AMFM. This step (AMFM) may increase the dimensionality, as we can perform filtering on the input image an arbitrary number of times (i.e., the depth, or number of channels may extend to infinity). Once the final feature set for $D_0$ is established (i.e., after any number of preprocessing steps including AMFM processing), feature set $D_{0,P}$ (which could very well be $D_P$ if no AMFM step is performed or example) is sent as input to an autoencoder. A function of the autoencoder is to compress feature set $D_{0,P}$ into an encoded space $E_0$ that is in a lower dimension (i.e., a smaller numerical feature vector, or numerical matrix) than $D_{0,P}$, and from $E_0$ to be able to reconstruct the original input, with some previously established loss (e.g., 100%, 90%, 80%, 70%, 60%, 50%, 40%, 30%, 20%, 10%, 5%, 2%, 1% reconstruction). This autoencoding process is iterative, in that feedback from the loss function (e.g., the absolute difference between the input feature vector $D_{0.P}$ and its reconstructed counterpart, $D_{o.P}'$) is sent as an input parameter into our subsequent iteration of the autoencoding process. There are a variety of optimizers, mostly centered around some version of gradient descent, but it is evident that any number of learning functions, optimizers, and hyperparameters (e.g., batch size, iterations, epochs) can be used.

Figure 2:
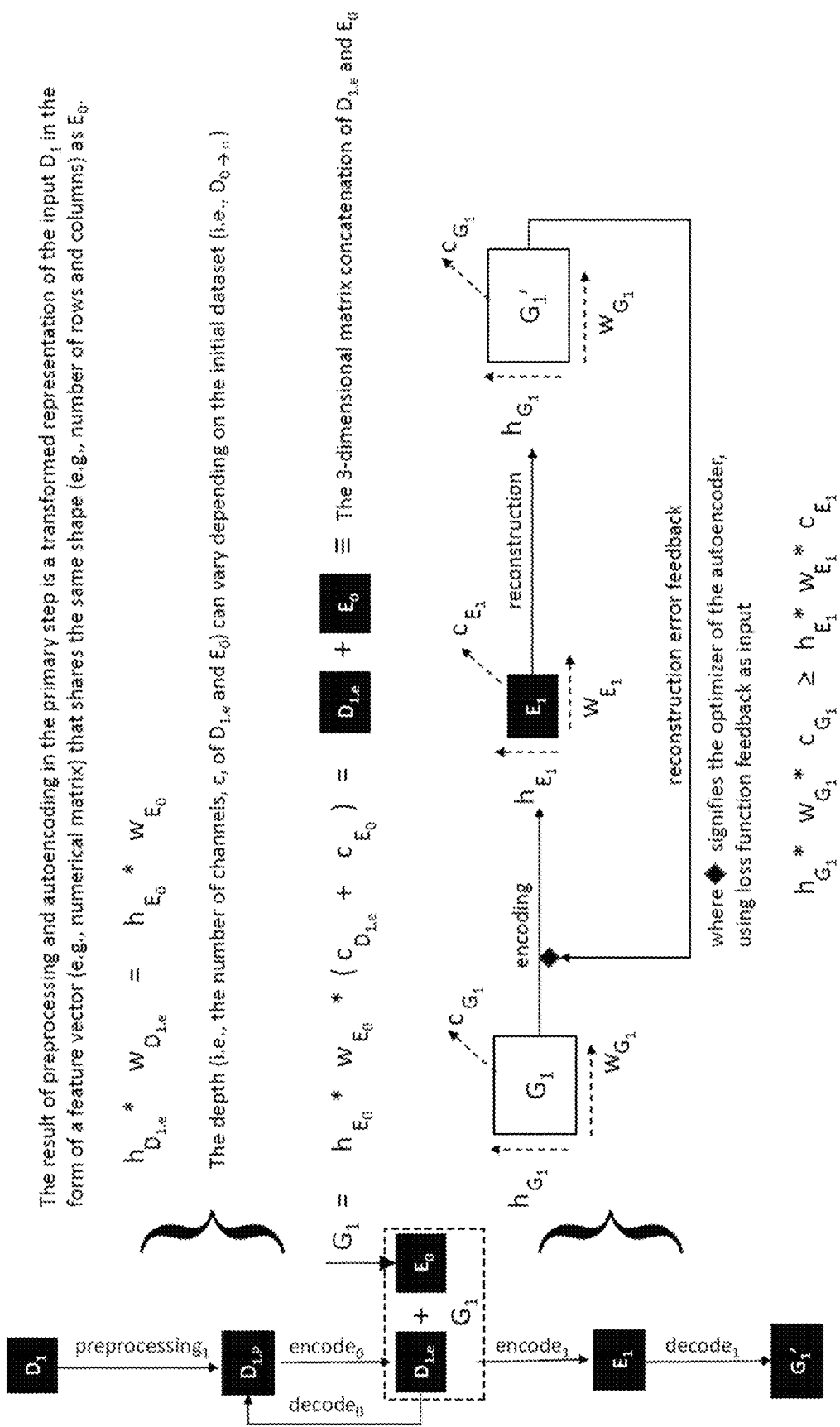
FIG. 2 illustrates one embodiment of a system for processing data sets obtained by a data capture device using a stacked autoencoder for standardizing the datasets.

Referring now to FIG. 2 a method of encoding the feature vector according to one embodiment of the present invention is illustrated. This method can be applied in a recursive manner for any lower level. For example, the layers of the stacked autoencoder are built from the bottom up. The method transforms a dataset $D_1$ into a feature vector (i.e., 3-dimensional numerical matrix) $D_{1.e}$ that is of the same shape as $E_0$. For example, the width and height of $D_1$ is equal to the width and height of $E_0$. The depth, or number of channels in the feature vector $D_{0.P}$ can vary (due to the number of examples in the initial datasets, as well as the preprocessing operations). The now-same-shaped feature vectors $D_{1.e}$ and $E_0$ (identical as to width and height but channels can be different or can be the same) are grouped via matrix concatenation. The result of this operation is a combined feature vector $G_1$ of the same shape, with depth equal to the sum of the depths of the two feature vectors $D_{1.e}$ and $E_0$. (The combined feature vector, or group $G_1$ is now ready to be fed to an autoencoder comprising encode1, with output $E_1$ decode$_1$ with output $G_1'$ and, with the goal of representing $G_1$ in $E_1$, where the dimensionality (i.e., shape and size) of $E_1$ is less than or equal to that of $G_1$. The cyclic process is the same as FIG. 1 autoencoding process, with the caveat that hyperparameters of the learning can be altered (i.e., it doesn't have to be the same autoencoder as the level above). Other encoding processes are known in the art and are applicable to processing the images with these encoding methods.

Figure 3:
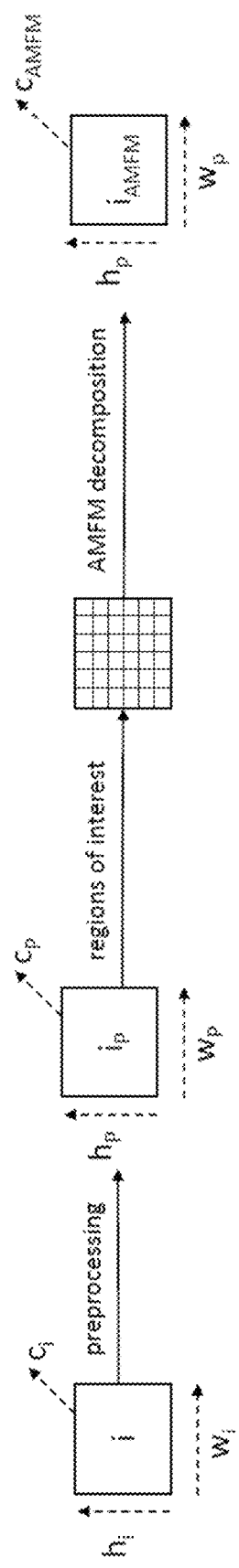
FIG. 3 illustrates one embodiment of a processing method for a data set having dimensions $w_i$, $h_i$, and $c_i$ according to one embodiment of the present invention.

Referring now to FIG. 3, a stacked autoencoder is illustrated according to one embodiment of the present invention. An input "i" of particular dimension (e.g., a 3-color channel retinal image of width "w" and height "h") is preprocessed (e.g., resized, color-corrected, histogram equalized, background subtracted, interpolated, etc.). Then, regions of interest are selected (i.e., the image is treated as a set of n-by-m smaller images, where n and m are the width and height of the windows). For each region of interest, the region of interest is processed with AMFM, which returns the instantaneous amplitude and instantaneous frequency angle and magnitude for the region of interest. The region of interest is defined by a group of tunable parameters set in the decomposition function that defines the dimension, number, and location of the original image to sample according to one embodiment of the present invention. The result is an AMFM decomposed copy of the preprocessed input, with number of channels equal to the number of AMFM decompositions. AMFM steps through one or more filters (for example a series of filters) designed to highlight particular anatomical/physiological aspects of the retinal image, and can be repeated any number of times. Note that the resulting channels can be a combination of AMFM scales, in any order.

Figure 4:
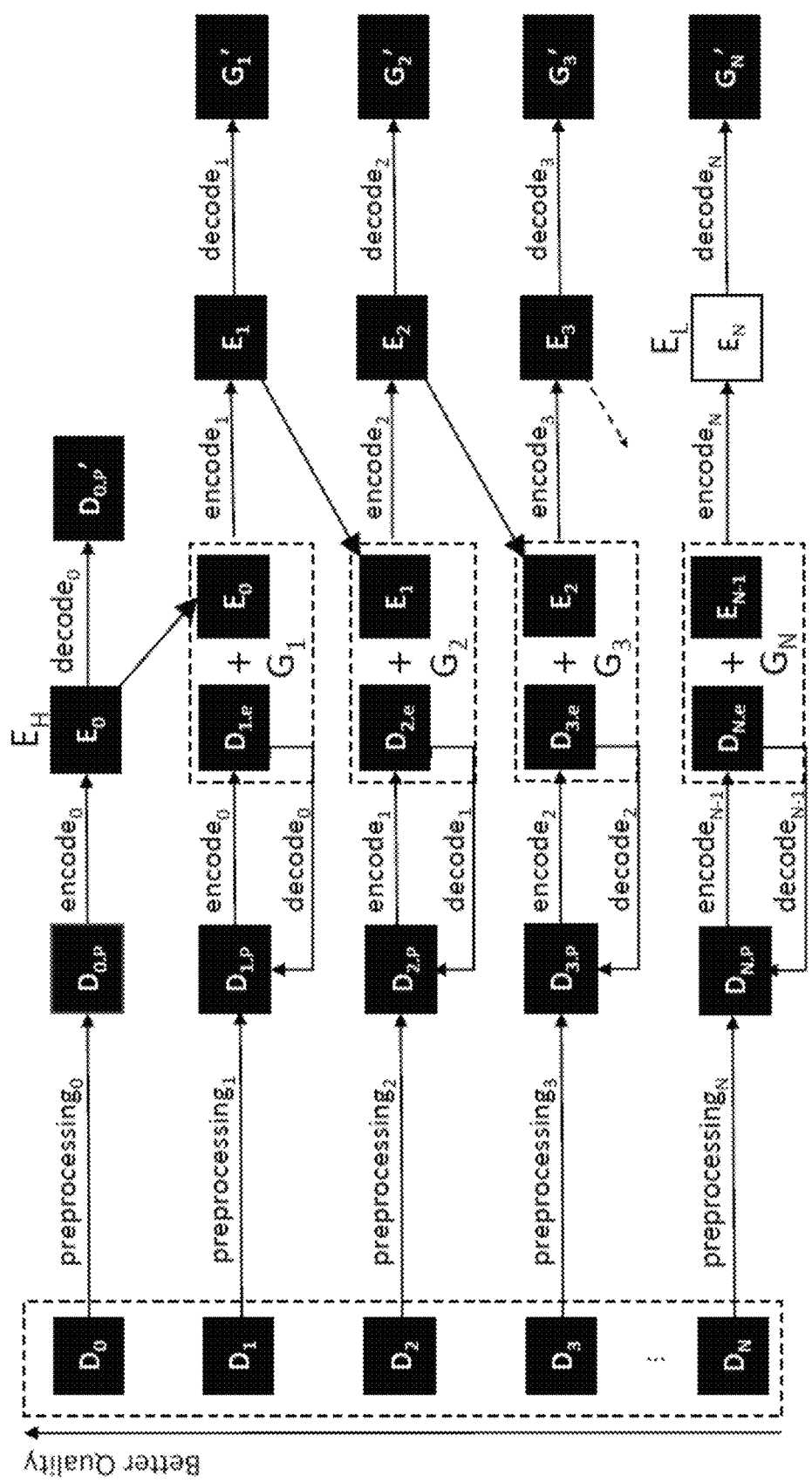
FIG. 4 illustrates an embodiment of a multilayer ($D_0$-$D_N$) stacked autoencoder according to one embodiment of the present invention.

Referring now to FIG. 4 a flow chart for processing images according to one embodiment of the present invention is illustrated. Datasets D (from 0 to N) exist. For each dataset, preprocessing is performed (e.g., AMFM, or other types of changes like resizing, down sampling, cropping, etc) to produce "$D_{0.P}$". Thereafter, the autoencoding process (e.g., multiple autoencoders, or stacked autoencoders) work with the preprocessed feature space and learn hidden representations, or encodings of the data "$E_0$". This autoencoding process is accomplished via loss functions that use the reconstruction error of the input as a means of iteratively updating the parameters needed to transform the input feature space into the encoded space (denoted E). At the 0 level the $E_0$ encoded image can be decoded $D_{0.P'}$ or encoded data can be used at the $D_1$ layer with encoder $D_{1.e}$. as shown in $G_1$. More formally, the preprocessed feature set from $D_1$, called $D_{1.P}$ is transformed to the same dimensionality as $E_0$. This process relies on autoencoding, wherein the input feature set $D_{1.P}$ is encoded to $D_{1.e}$. A decoded reconstruction of the input feature set, $D_{1.P}'$ (not depicted, but equivalent to $D_{0.P}'$), is compared against the original input (via a plurality of techniques), and a difference (again, via a plurality of techniques) is computed. Figure A highlights the feedback loop used in the cyclic autoencoding process. When moving to the next level (i.e., stepping down one layer), the encoded features from above are passed down and treated together with the current level's encoded bits, and is denoted as a group $G_n$ where n is an integer, for example $G_1$. Another round of autoencoding is performed with the group at the box labeled $G_1$ having both $D_{2.e}$ and $E_0$. The encoded image $E_1$ is stepped down another layer and/or $E_1$ can be decoded to $G_1'$. When $E_1$ is stepped down to the lower layer, $E_1$ is combined with $D_{2.e}$ to form the group $G_2$. The process repeats until reaching the final layer N, where we ultimately arrive at the lowest representation of our data, $E_L$ having arrived at the lowest encoded feature set, handling the lowest fidelity data set from the lowest fidelity data capturing device.

Figure 5:
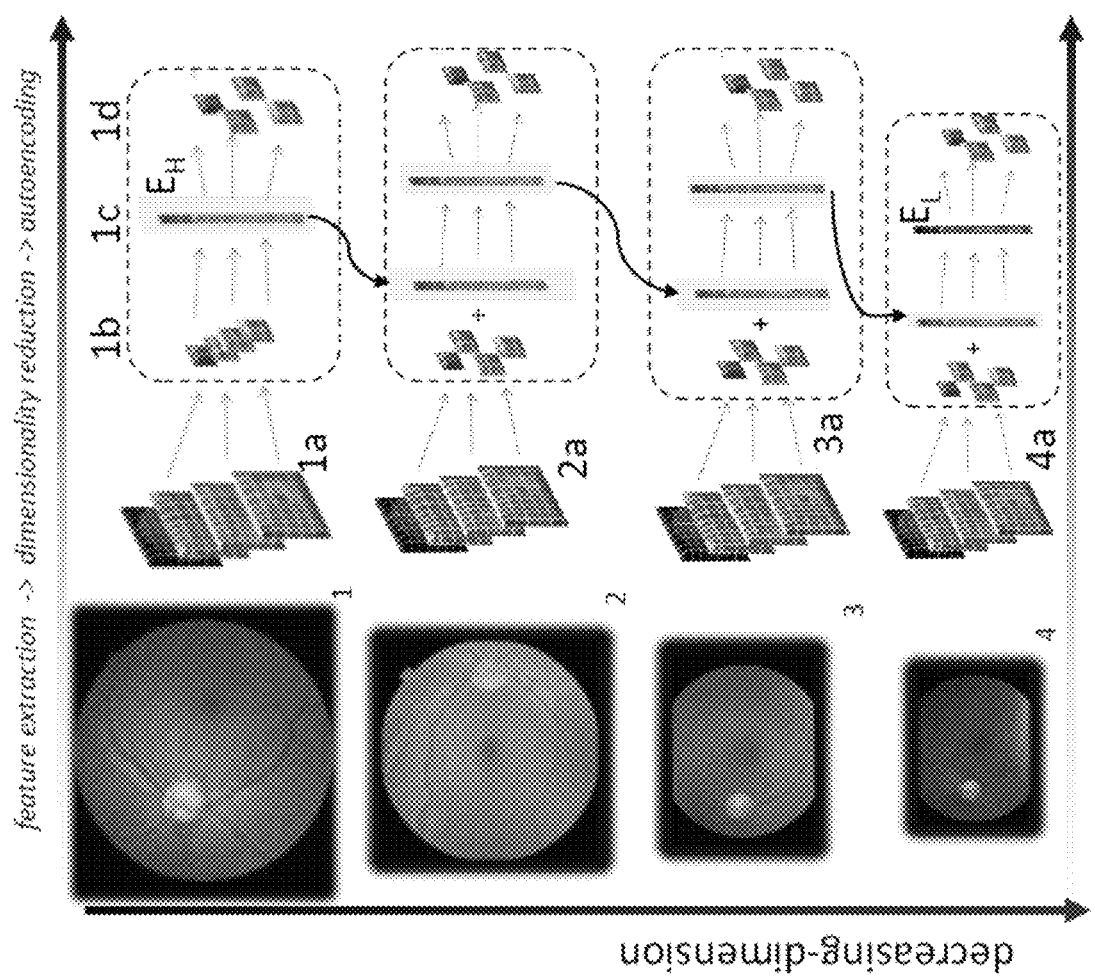
FIG. 5 illustrates a system and method of one embodiment of the present invention for transformation of retinal images wherein $E_H \gg E_L$ and wherein "E" is encoded "H" is highest level; "M" is middle level (worse than the level above and better than the level below); "L" is lowest level wherein $E_H > E_M > E_L$; the encoded bits at the highest level (best camera quality) is the largest (dimension/size) and the encoded bits at the lowest level (worst camera quality) are the smallest (i.e., our least common denominator)

Referring now to FIG. 5, a particular application of the method for image transformation in retinal image analyses is illustrated. The datasets are images from a variety of data capture devices such as cameras. Similar to FIG. 4, a first step in the process is a feature extraction 1a (here, represented as a shift into a 4 channel AMFM decomposition for example, and subsequently into a pooling or downsizing phase 1b. The preprocessed data is then treated as input 1b into the autoencoder (e.g., a stacked autoencoder, a convolutional autoencoder, a denoising autoencoder, etc). The reconstruction error is computed between the output of the autoencoder 1d and its input 1d-1b. For the next level 2, the encoded features ($E_H$) from the layer above are incorporated into level 2's autoencoding process. The bottom-most layer is ultimately achieved, where $E_L$ represents the lowest representation of the encoded data (for example bits at the lowest dimension). As it relates to the reconstruction error, the dataset can be reconstructed to a percent of the original in terms of features within the dataset (i.e. when the dataset is an image of the eye and reconstruction is of one or more of the following: histograms in R, G, B color channels, optic disc/fovea location, vessel structure, root mean squared error (between original and reconstructed image), absolute difference pixel-wise).

It should be noted that the top layer in FIG. 5 handles retinal images of highest dimensionality from a state-of-the art camera with the highest resolution, dimensionality, and physiological field of view (e.g. CR2-AF or similar) and may be considered images captured from a high fidelity camera. The bottom layer handles retinal images from lower specification handheld cameras (e.g. Volk Pictor Plus or similar) and may be considered images captured from a low fidelity camera whose images have lower resolution, dimensionality, and field of view. Intermediate layers are designed to support retinal images from cameras whose specifications fall somewhere in between.

The AM-FM filters are a multiscale filterbank with bandpass filters that correspond to each scale that are used to calculate estimates for instantaneous amplitude and instantaneous frequency and are used in discriminating between normal and pathological retinal images [11]. In one embodiment of the present invention, the AM-FM filters are used as the first step or layer in the stacked autoencoders' architecture. It shall be evident to those skilled in the art that other filtering methods, such as wavelets, Gabor, or those that arise from machine learning algorithms can be used interchangeably as part of the stacked autoencoder.

Figure 6:
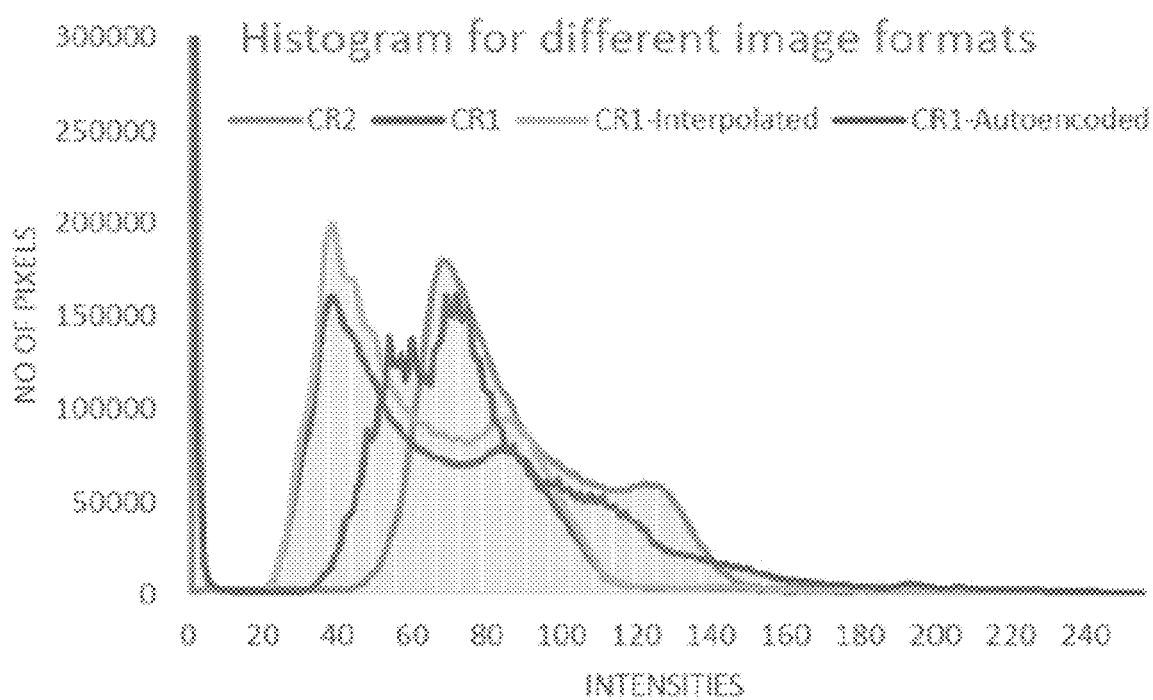
FIG. 6 illustrates a histogram for different image formats for image CR1 and CR2.

Referring now to FIG. 6 a histogram for different image formats is illustrated wherein pixels on the Y axis are compared to intensities for each image format.

Figure 7:
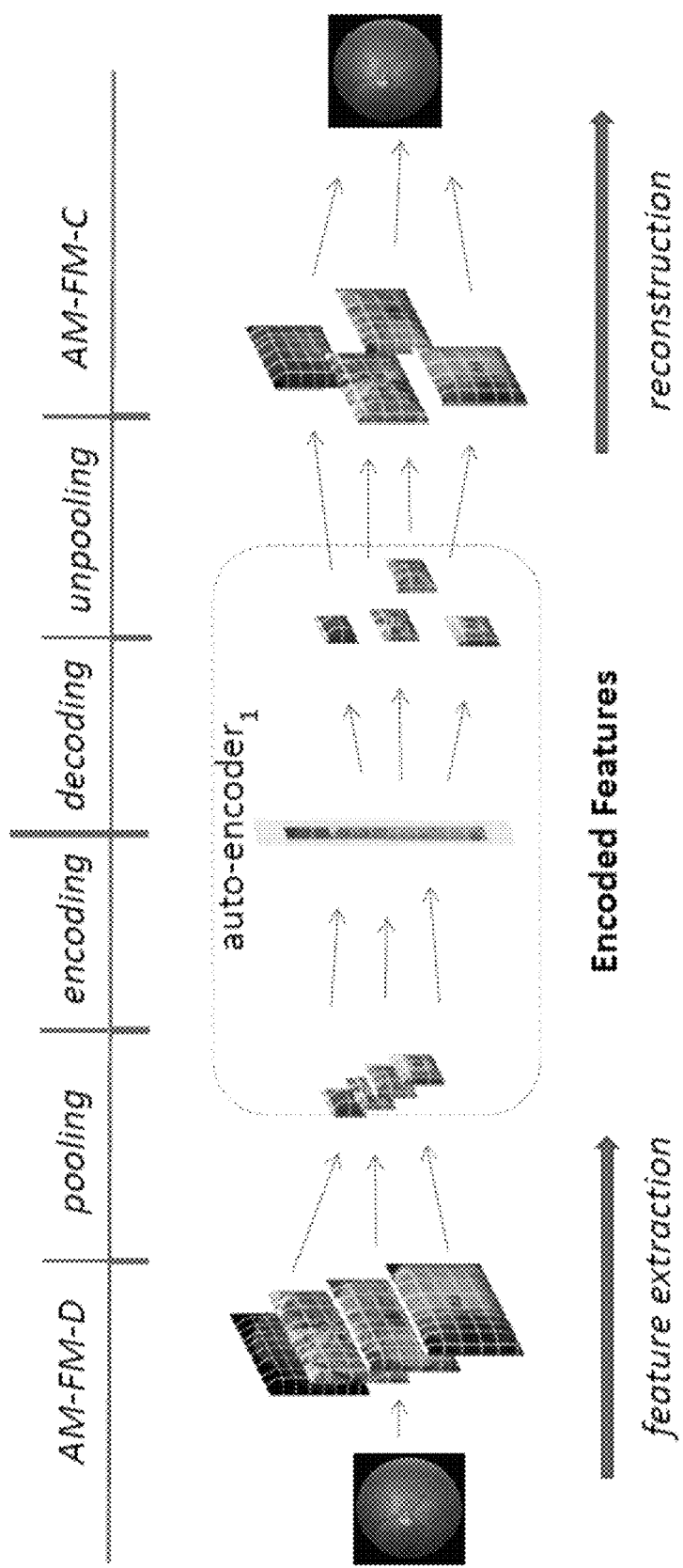
FIG. 7 illustrates a flow chart of a method for processing a medical image with an autoencoder according to one embodiment of the present invention.

Referring now to FIG. 7, an encoding method according to one embodiment of the present invention is applied to retinal images. The image obtained by a camera that captures images having a low fidelity data set is processed using a feature extraction step such as AMFM to produce a processed feature set at the feature extraction step. The processed feature set is pooled and serves as the input for the auto-encoders comprising the steps of encoding and decoding. The encoded feature set is unpooled and reconstructed using an AMFM step, for example.

Figure 8A:
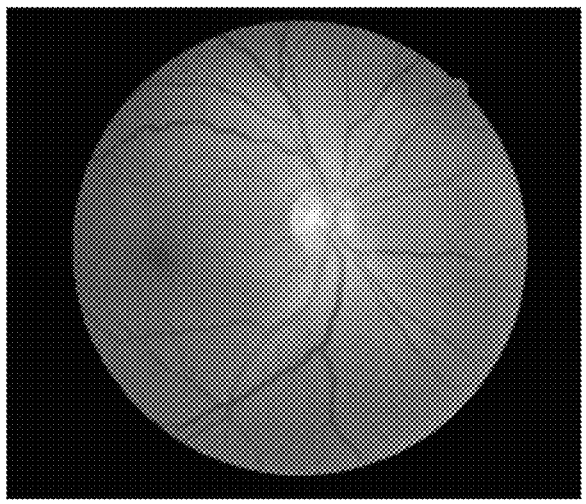
FIG. 8 A-B illustrates an image that is an example of the encoded feature set of the image transformed with a system and method according to one embodiment of the present invention in using two retinal images of different characteristics, wherein the lowest fidelity encoded feature sets are representative of the original images.
Figure 8B:
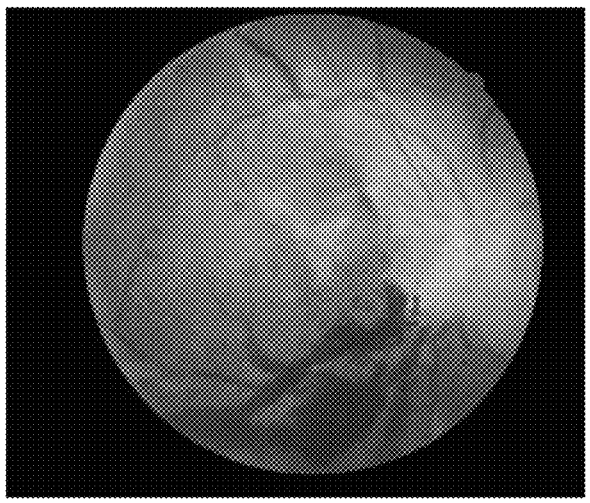

Regarding FIG. 8A and FIG. 8B, the lowest fidelity's ultimate encoded feature set for each image is illustrated according to an exemplary processing of the images with an encoder system and method as discussed herein. An example 'encoding' of these images are in the following encoded feature set wherein FIG. 8A is the left image with no pathology and having the encoded feature set [0000110000000011]. FIG. 8B is the image on the right with pathology and having the encoded feature set [1011111110011111]. A plurality of images obtained with a variety of imagers having different fidelity will make up a database of images. Given sufficient examples in each class (i.e., with or without pathology), these encoded feature sets would group or cluster into the same set or bucket. That is, other images with no pathology would have similar vectors. This grouping expands/grows to N number of classes. Thus auto-encoding produces more classes than what humans would typically label. Further still an encoded feature set could be used to index and/or sort the information and be treated as encrypted while still being mappable to the original image.

According to one embodiment of the present invention, the training process of the deep neural network method is a two-step process: 1) training, and 2) fine-tuning. The unsupervised pre-training is performed one layer at a time. The retinal images from different cameras are used as inputs to train at different layers. The top level is trained with images from the state-of-the art fundus camera; it is autoencoded until it reaches a reconstruction (or decoding) point by minimizing error in the reconstruction of its input, handled by a cost function. An example of cost function comprises of cross-entropy cost, quadratic cost, exponential cost, etc. Another cost function comprises modified mean square error function. It shall be evident to others skilled in the art that other cost functions can also be used for training the present invention. A plurality of activation functions can be used in this deep neural network. An example of activation function comprises Logistic sigmoid, rectified linear unit (ReLU), leaky ReLU, exponential linear unit (eLU) etc. It shall be evident to others skilled in the art that other forms of activation functions can also be used as part of the present invention. Then, the next layer of the stack is trained with images from another camera in a similar way, except with the added features from the layer above. Each layer is trained by minimizing error in the reconstruction of its input.

In one embodiment, the layers are individually trained (i.e., each layer has no information about the other layers), and are joined together to form a deep neural network. A particular layer is, at any time, subject to manual, fine-tuning, to optimize architecture and accuracies. The lowest dimensional feature space at the bottom-most layer is the target for all layers above. Any manual fine-tuning updates for each layer's architecture will maximize the reconstruction from the input of the training phase, whilst incorporating the hidden features from the layer above. In one embodiment, after the deep network is trained, there will be no need to retrain or redesign the network.

A plurality of image representations can be used with the present invention. In one embodiment of the present invention, three separate deep neural networks for three color channels (red channel, green channel and blue channel) can be used to determine a plurality of eye diseases.

The lowest dimensionality feature set obtained from the bottom layer's SAE is used as an input to a classifier or multiple classifiers trained to detect a plurality of retinal pathologies. One embodiment of present invention comprises detection of DR into one of two classes: "Referral DR" if the image presents with moderate or severe level of DR and "No Referral" if the image presents characteristics of mild or no DR. Other embodiments of the present invention comprise determination of DR into more than two levels according to a pre-defined grading scale. It shall be evident to anyone skilled in the art that the same phases can be applied to determine other eye diseases alone or in combinations.

One aspect of one embodiment of the present invention uses a classifier based upon using Multi-class support vector machines (Multi-class SVM) [25]. Tang et al. [26] have demonstrated the advantage of using support vector machine over the softmax activation function, commonly used in deep learning models. It will be evident to one skilled in the art that a plurality of other classifiers can also be used without changing the scope of the embodiment as disclosed herein, including but not limited to the support vector machines (SVM), K-Nearest Neighbor (kNN), linear classifier, an ensemble of convolutional neural networks (CNN), and recurrent neural networks (RNN).

One embodiment of the present invention is used for AMD detection and classification. The images are classified as "No Referral/0" (No AMD, AREDS category 1) and "Referral/1" (AMD AREDS category 2, 3 and category 4) [27].

One embodiment of the present invention can be used for classifying the following retinal pathologies: dry and wet AMD, hypertensive retinopathy, Branch Retinal Vein Occlusion (BRVO), Central Retinal Vein Occlusion (CRVO), Branch Retinal Artery Occlusion (BRAO), Central Retinal Artery Occlusion (CRAO), Central Serous Chorioretinopathy (also known as Central Serous Retinopathy), Epiretinal Membranes, Retinitis, Macula Edema, Cystoid Macula Edema, Macular Hole, Chorioretinitis, Presumed ocular histoplasmosis syndrome, Toxoplasmosis, Multifocal Choroiditis, Retinal Detachment/Tear, Retinitis Pigmentosa, Retinopathy of Prematurity, Stargardt disease, fundus albipunctatus, retinitis *punctata albescens*, best disease, gyrate atrophy, cone dystrophy, rod-cone dystrophy, choroideremia, choroidal nevus, choroidal melanoma, choroidal hemangioma, congenital hypertrophy of retinal pigment epithelium (CHRPE), chloroquine toxicity, tamoxifen toxicity, angioid streaks, polypoidal choroidal vasculopathy (PCV), leukemic retinopathy, radiation retinopathy, Cytomegalovirus (CMV) Retinitis, systemic lupus erythematosus (SLE), Vogt-Koyanagi-Harada (VKH) syndrome, Behcet's disease, giant cell arteritis (GCA), solar retinopathy, sickle cell retinopathy, sarcoidosis, shaken baby syndrome, commotio retinae, choroidal rupture, birdshot chorioretinopathy, X-linked juvenile retinoschisis. It shall be evident to others skilled in the art that the present invention can be used to determine the presence and grade of presentation of other eye diseases not limited to the ones listed herein.

An example of an aspect of one embodiment of the present invention comprises the construction of layered SAEs with a database of over 250,0000 images from eleven camera models (Canon CR1, Canon CR2, Canon, CF-60UV, Centervue DRS, Topcon TRC NW6, Topcon TRC 50EX, Welch Allyn RetinaVue, Zeiss VISUCAM, Forus 3nethra, Horus Scope and Volk Pictor). In order to demonstrate the robustness of the model in terms of its ability to work with new camera types, an example training and validation is as follows: The framework is trained with images from six different camera models and the validation set consists of images from the remaining camera models. Training means that the framework is built using only images from these camera models, and the final encoded feature space is clinically viable as input to a classifier (for example, the sensitivity and specificity of identifying diabetic retinopathy are both above 80%). Validation means sending images from previously unused camera models through the framework and ensuring that the final classification maintains its level of performance (i.e., 80%). It shall be evident to others skilled in the art that the utility of the present invention is not limited to these 11 cameras and that a plurality of available cameras can be used herein without modification. Camera differences may include resolution (size, shape, width, height); dimension (pixel density, pixel per micron); compression (how corrupted is the data when the data is transferred from the camera to a computer for example; file size); color channel intensities (histograms of Red, Green Blue channels) and hardware (flash, led, optics) for example.

Note that in the specification and claims, "about" or "approximately" means within twenty percent (20%) of the numerical amount cited. All computer software disclosed herein may be embodied on any computer-readable medium (including combinations of mediums), including without limitation CD-ROMs, DVD-ROMs, hard drives (local or network storage device), USB keys, other removable drives, ROM, and firmware.

Although the invention has been described in detail with particular reference to these embodiments, other embodiments can achieve the same results. Variations and modifications of the present invention will be obvious to those skilled in the art and it is intended to cover in the appended claims all such modifications and equivalents. For example, one embodiment comprises a system comprising an imager or camera and a computer wherein the computer has a processor arranged and or programmed for training a neural network or arranged to use a trained neural network that receives a plurality of input data sets or images from the imager or camera and standardizes the plurality of data sets via an autoencoder as described herein wherein the output (encoded feature set) is used for further analysis with a classifier that automatically classifies the encoded feature sets and or data sets and/or images as disclosed herein. The entire disclosures of all references, applications, patents, and publications cited above are hereby incorporated by reference.

The invention claimed is:

1. A method of standardizing a plurality of data sets obtained from an arbitrary number of data capturing devices comprising the steps of:
    processing a first data set obtained from a first data capturing device with a first feature extraction process to produce a first processed feature set wherein the first data capturing device captures a first data set at a low fidelity level;
    encoding the first processed feature set to produce a first encoded feature set;
    processing a second data set from a second data capturing device with a second feature extraction process which may be the same or different from the first feature extraction process to produce a second processed feature set wherein the second data capture device captures the second data set at a high fidelity level as compared to the low fidelity level of the first data set; and
    encoding the second processed feature set to produce the second encoded feature set wherein the second encoded feature set is constrained by the first encoded feature set such that the second encoded feature set is of a same or greater dimensionality as compared to the first encoded feature set.

2. The method of claim 1 wherein the first data set is a digital image.

3. The method of claim 1 wherein the second data set is a digital image.

4. The method of claim 1 wherein the first feature extraction process includes AMFM.

5. The method of claim 1 wherein the second feature extraction process includes AMFM.

6. The method of claim 1 wherein the low fidelity level includes decreased image characteristics selected from the group consisting of pixel count, resolution, dimensionality.

7. The method of claim 1 wherein the encoding step compresses the first processed feature set into an encoded space that is in a lower dimension than the first processed feature set.

8. The method of claim 1 wherein the encoding step compresses the second processed feature set into an encoded space that is in a lower dimension than the second processed feature set.

9. The method of claim 1 wherein the processing step comprises reducing the dimensionality of the first data set wherein the dimensionality includes a row, a column and a depth of a numerical matrix.

10. The method of claim 1 wherein the encoding process is iterative such that a loss function is sent as an input parameter to a subsequent iteration of the encoding step.

11. The method of claim 1 wherein the first data capturing device is an imager.

12. The method of claim 11 wherein the imager is a digital camera.

13. The method of claim 1 wherein the second data capturing device is an imager.

14. The method of claim 13 wherein the imager is a digital camera.

15. A method of standardizing a plurality of digital images of a retina for use with an automated retinal disease classifier comprising:
    processing a first digital retinal image obtained from a first imager with a first feature extraction process to produce a first processed feature set wherein the first data imager captures a first digital retinal image data set at a low fidelity level;

encoding the first processed feature set to produce a first encoded feature set;

processing a second digital retinal image obtained from a second imager with a second feature extraction process which may be the same or different from the first feature extraction process to produce a second processed feature set wherein the second imager captures the second digital retinal image at a high fidelity level as compared to the low fidelity level of the first data set; and encoding the second processed feature set to produce a second encoded feature set wherein the second encoded feature set is constrained by the first encoded feature set such that the second encoded feature set is of a same or greater dimensionality as compared to the first encoded feature set.

16. The method of claim 15 further comprising classifying the first encoded feature set and the second encoded feature set for the presence or absence of a retinal disease with a classifier such that the disease is classified with a sensitivity and/or specificity of about 80% or better.

* * * * *